(12) United States Patent
Steiniger et al.

(10) Patent No.: US 8,853,465 B2
(45) Date of Patent: Oct. 7, 2014

(54) PROCESS FOR PREPARING NEOPENTYL GLYCOL

(75) Inventors: Michael Steiniger, Neustadt (DE); Maria Guixa Guardia, Mannheim (DE); Kai Stehmeier, Mannheim (DE)

(73) Assignee: BASF SE, Ludwigshafen (DE)

( * ) Notice: Subject to any disclaimer, the term of this patent is extended or adjusted under 35 U.S.C. 154(b) by 393 days.

(21) Appl. No.: 13/105,271

(22) Filed: May 11, 2011

(65) Prior Publication Data

US 2011/0282106 A1 Nov. 17, 2011

Related U.S. Application Data

(60) Provisional application No. 61/333,762, filed on May 12, 2010.

(51) Int. Cl.
*C07C 29/141* (2006.01)
*C07C 45/75* (2006.01)

(52) U.S. Cl.
CPC ............... *C07C 29/141* (2013.01); *C07C 45/75* (2013.01)
USPC ............................ 568/862; 568/846; 568/861

(58) Field of Classification Search
USPC .......................................... 568/846, 861, 862
See application file for complete search history.

(56) References Cited

U.S. PATENT DOCUMENTS

| | | | |
|---|---|---|---|
| 4,122,290 A | 10/1978 | Immel et al. | |
| 4,247,485 A | 1/1981 | Immel et al. | |
| 4,386,219 A | 5/1983 | Merger et al. | |
| 6,018,074 A | 1/2000 | Kratz et al. | |
| 6,187,971 B1 | 2/2001 | Kratz et al. | |
| 6,201,160 B1 | 3/2001 | Brudermuller et al. | |
| 7,462,747 B2 * | 12/2008 | Sirch et al. | 568/799 |
| 2003/0009062 A1 | 1/2003 | Dobert et al. | |
| 2006/0205985 A1 | 9/2006 | Wartini et al. | |
| 2009/0069604 A1 * | 3/2009 | Maas et al. | 568/465 |
| 2011/0184212 A1 * | 7/2011 | Schulz et al. | 568/852 |

FOREIGN PATENT DOCUMENTS

| | | |
|---|---|---|
| CN | 1328986 A | 1/2002 |
| DE | 1957591 A1 | 5/1971 |
| DE | 2702582 A1 | 7/1978 |
| DE | 2813201 A1 | 10/1979 |
| EP | 0044444 A1 | 1/1982 |
| JP | 2004-182622 A1 | 7/2004 |
| WO | WO-97/17313 A1 | 5/1997 |
| WO | WO-98/28253 A1 | 7/1998 |
| WO | WO-98/29374 A1 | 7/1998 |
| WO | WO-01/51438 A1 | 7/2001 |
| WO | WO-2004/092097 A1 | 10/2004 |
| WO | WO-2007/042456 A1 | 4/2007 |
| WO | WO-2007/099064 A1 | 9/2007 |
| WO | WO-2010/066673 A2 | 6/2010 |
| WO | WO-2010/066674 A2 | 6/2010 |
| WO | WO-2010/079187 A1 | 7/2010 |

* cited by examiner

*Primary Examiner* — Sudhakar Katakam
*Assistant Examiner* — Pancham Bakshi
(74) *Attorney, Agent, or Firm* — Drinker Biddle & Reath LLP

(57) ABSTRACT

The present invention relates to a process for preparing neopentyl glycol (NPG) by continuously hydrogenating hydroxypivalaldehyde (HPA) with hydrogen, in the liquid phase, in the presence of a hydrogenation catalyst, in a hydrogenation reactor (5), by combining an HPA-comprising stream (1) with an NPG-comprising stream (2) to give a hydrogenation feed (4) and introducing the hydrogenation feed (4) into the hydrogenation reactor (5) and additionally supplying at least one pH regulator (3) selected from the group consisting of tertiary amine, an inorganic base, an inorganic acid and an organic acid to the HPA-comprising stream (1) or the NPG-comprising stream (2) or the hydrogenation feed (4), in order to establish a pH of 7.0 to 9.0 at the outlet of the hydrogenation reactor, wherein the weight ratio of HPA to NPG in the hydrogenation feed (4) is in the range from 1:100 to 50:100 and the proportion of HPA and NPG in the hydrogenation feed (4) is at least 50% by weight, based on the hydrogenation feed, and, in the case that the pH regulator (3) is supplied to the HPA-comprising stream (1), the HPA-comprising stream (1) comprises less than 50% by weight of HPA or the residence time between the supply of the pH regulator (3) and the combining of the NPG-comprising stream (2) with the HPA-comprising stream (1) is less than 5 minutes or the temperature of the HPA-comprising stream (1) is less than 75° C.

9 Claims, 6 Drawing Sheets

PROCESS FOR PREPARING NEOPENTYL GLYCOL

RELATED APPLICATIONS

This application is a non-provisional utility application which claims benefit of U.S. Provisional Patent Application Ser. No. 61/333,762. filed May 12, 2010.

The present invention relates to a process for preparing neopentyl glycol (NPG) by hydrogenating hydroxypivalaldehyde (HPA).

Neopentyl glycol is used as a raw material for the preparation of saturated polyester resins for powder coatings, and for glass fiber-reinforced plastics.

Neopentyl glycol is generally prepared in a two-stage process in which isobutyraldehyde (IBA) is first reacted with formaldehyde (FA) in an aldol addition to give hydroxypivalaldehyde, which can be hydrogenated in a second process stage directly to NPG.

In the first process stage (aldol reaction), isobutyraldehyde is generally reacted in an aldol reaction with formaldehyde in the presence of tertiary amines as a catalyst.

The discharge from the aldol reaction comprises typically HPA and unconverted starting compounds, such as formaldehyde, IBA, and also the tertiary amine catalyst used and water.

The discharge typically also comprises impurities and by-products from the aldol reaction, such as formic acid, which can form from formaldehyde by Cannizzaro or Tishchenko reaction, and formate salts of the amine catalysts used, such as trimethylammonium formate.

After the aldolization, unconverted aldehydes and a portion of the amine base are generally removed by distillation and recycled into the aldol reaction.

In the distillation bottoms there typically remain HPA, water, trialkylammonium formate and formic acid. Formic acid is generally formed in the aldolization as a by-product in a Cannizzaro reaction from formaldehyde. The distillation bottoms therefore generally have an acidic pH (pH<7).

In general, the discharge from the column bottom is passed as a mixture to be hydrogenated into a hydrogenation reactor and hydrogenated over a heterogeneous catalyst in the presence of hydrogen to give NPG.

In order to reduce the formation of by-products and in order to prolong the service life of the catalyst and to avoid a rapid decrease in activity of the catalyst, the prior art teaches that the pH of the mixture from the aldolization to be hydrogenated should be adjusted to a particular pH range.

For instance, WO-A-2004092097 discloses a hydrogenation process in which addition of a tertiary amine to the mixture from the aldolization to be hydrogenated establishes a pH in this mixture of 6.3 to 7.8.

WO-A-2007099064 additionally discloses that a multitude of side reactions which can alter the pH in the hydrogenation reactor take place during the hydrogenation reaction.

For example, formic acid which is formed in the aldolization as a by-product via a Cannizzaro reaction from formaldehyde is decomposed during the hydrogenation catalytically to $CO_2$ and $H_2$ or to CO and $H_2O$. The decomposition rate of the undesired formic acid by-product depends not only on the temperature but also crucially on the age of the catalyst. With increasing age of the catalyst, the decomposition rate of formic acid also decreases permanently under constant reaction conditions.

Therefore, the pH in the reactor does not correlate with the pH of the hydrogenation feed from the aldolization. The difference of the pH values between feed and discharge is influenced by a multitude of unpredictable factors, such as the activity of the catalyst with respect to the decomposition of formic acid, and by temperature, offgas rate and catalyst hourly velocity.

WO-A-2007099064 additionally teaches that the extent and the rate of different side reactions which take place during the hydrogenation are dependent on the pH in the hydrogenation reactor.

For example, the retro-aldol reaction and the Tishchenko reaction increase significantly at high pH values.

In the retro-aldol reaction, the methylolalkanals are generally cleaved to the corresponding starting aldehydes, which are hydrogenated to undesired by-products (in the NPG preparation, this forms isobutanol and methanol). This correspondingly reduces the yield in the hydrogenation.

The Tishchenko reaction of methylolalkanals leads to the formation of the corresponding methylol methylolalkanolates. For example, neopentyl glycol hydroxypivalate (NHP) is formed from hydroxypivalaldehyde (HPA), which hydrolyzes partly to NPG and hydroxypivalic acid (HPAC), which in turn leads to a lowering of the pH and of the selectivity.

In addition, acetals can form during the hydrogenation. In the case of the NPG synthesis, the formation of the cyclic acetal of NPG and hydroxypivalaldehyde (HPA) is also observed to an enhanced degree at elevated temperature. This by-product cannot be separated by distillation from NPG and therefore leads to a less pure product of value. The acetal formation is also pH-dependent.

To reduce side reactions and to improve the selectivity in the hydrogenation, WO-A-2007099064 teaches the establishment of a pH of 7.0 to 9.0 in the hydrogenation output. The pH in the hydrogenation output is adjusted by adding at least one tertiary amine, an inorganic base, an inorganic acid or an organic acid to the mixture from the aldolization to be hydrogenated.

JP-A-2004182622 describes a hydrogenation process in which the pH in the mixture from the aldolization to be hydrogenated is adjusted to a pH of 5.5-7.5, in order to reduce discharge of the active metal from the catalyst at lower pH values, since the discharge of active metal leads to a continuous loss of catalyst activity, and metal traces are disruptive in the further workup. At higher pH values, aldol condensations which reduce the selectivity of the process were observed.

The prior art states that the pH regulators, for example tertiary amines, inorganic base, inorganic acid or organic acid, should be added to the mixture from the aldolization to be hydrogenated, in order to regulate the pH in the hydrogenation reactor.

Further technical details of the metered addition, especially with regard to the exact composition of the mixture from the aldolization to be hydrogenated before and after the metered addition of the pH regulator or the exact feed point, are not described explicitly in the disclosures mentioned.

In the context of the present invention, it has now been found that the hydrogenation of HPA can be improved further when an HPA-comprising stream, before being introduced into the hydrogenation reactor, is combined with an NPG-comprising stream, and when the conditions of combination of these streams and the conditions of supply of the pH regulator are combined with one another in a suitable manner.

It is an object of the present invention to provide an improved process for hydrogenating HPA, in which side reactions should be suppressed and both the yield and the selectivity should be further improved over the prior art hydrogenations. Moreover, the service life of the catalysts used in the hydrogenations should be increased further. In addition, the amount of the pH regulators added should be reduced in order to reduce the amount of the raw materials used.

The object of the present invention is achieved by a process for preparing neopentyl glycol (NPG) by continuously hydrogenating hydroxypivalaldehyde (HPA)
with hydrogen,
in the liquid phase,
in the presence of a hydrogenation catalyst,
in a hydrogenation reactor (5),
by combining an HPA-comprising stream (1) with an NPG-comprising stream (2) to give a hydrogenation feed (4) and introducing the hydrogenation feed (4) into the hydrogenation reactor (5)
and additionally supplying at least one pH regulator (3) selected from the group consisting of tertiary amine, an inorganic base, an inorganic acid and an organic acid to the HPA-comprising stream (1) or the NPG-comprising stream (2) or the hydrogenation feed (4),
in order to establish a pH of 7.0 to 9.0 at the outlet of the hydrogenation reactor,
wherein
the weight ratio of HPA to NPG in the hydrogenation feed (4) is in the range from 1:100 to 50:100 and
the proportion of HPA and NPG in the hydrogenation feed (4) is at least 50% by weight, based on the hydrogenation feed,
and, in the case that the pH regulator (3) is supplied to the HPA-comprising stream (1),
the HPA-comprising stream (1) comprises less than 50% by weight of HPA or
the residence time between the supply of the pH regulator (3) and the combining of the NPG-comprising stream (2) with the HPA-comprising stream (1) is less than 5 minutes or
the temperature of the HPA-comprising stream (1) is less than 75° C.

In the process according to the invention, an HPA-comprising stream and an NPG-comprising stream are combined. The combined streams are referred to in the context of the present invention as "hydrogenation feed". Accordingly, the term "hydrogenation feed" refers to the stream which results from the combination of the HPA-comprising stream with the NPG-comprising stream, and which is introduced into the hydrogenation reactor.

An HPA-comprising stream is used in the process according to the invention.

The HPA-comprising stream used is preferably a reaction discharge from the aldol reaction of isobutyraldehyde and formaldehyde.

Such a reaction discharge can be prepared, for example, according to the disclosure of WO-A-98/28253 or of DE-A-1957591 by reaction of IBA with formaldehyde. The procedure is generally such that the IBA used in the aldol reaction is reacted with 1 to 8 times the amount of formaldehyde in the presence of a tertiary amine (aldolization).

The tertiary amines used may be amines as described, for example, in DE-A 28 13 201 and DE A 27 02 582. Particular preference is given to tri-n-alkylamines, especially triethylamine, tri-n-propylamine, tri-n-butylamine and trimethylamine.

Very particular preference is given to trimethylamine (TMA), triethylamine (TEA) and tri-n-propylamine (TPA), since these compounds generally have a lower boiling point than the polymethylols formed preferentially, and hence the distillative removal from the reaction mixture is facilitated. Trimethylamine (TMA) is especially preferably used as the tertiary amine in the aldolization.

The reaction product is subsequently typically separated by distillation.

This involves supplying the discharge from the aldol reaction to a distillation apparatus, generally to a column, in which it is separated into more and less volatile constituents.

The distillation conditions are generally selected such that a fraction composed of low boilers forms, in which the significant components present are unconverted alkanal, with or without water, formaldehyde and methanol. In the case of use of trimethylamine (TMA) as the tertiary amine, the distillation conditions are selected that the TMA is also present partly in the low boiler fraction and to a small degree in the bottom product. In the case of use of triethylamine (TEA), the distillation conditions are selected such that TEA is enriched in the bottom product.

This so-called low boiler fraction can be recycled into the first stage of the hydrogenation process, the aldol reaction, or sent to a further workup stage.

After removal of the low boiler fraction, the distillative workup outlined leaves a relatively nonvolatile bottom product which consists essentially of HPA, water, formic acid and amine formate, which can be used as the HPA-comprising stream in the process according to the invention.

However, it is also possible to use an HPA-comprising stream which has been prepared by other prior art processes, for example the processes known from WO 01/51438, WO 97/17313 and WO 98/29374.

The HPA content in the discharge from the aldol reaction after removal of the low boiler fraction in a customary HPA-comprising stream is, according to the aforementioned disclosures, within a wide range from 20 to 95% by weight, preferably from 40 to 85% by weight and more preferably from 50 to 80% by weight.

The HPA-comprising stream from the aldolization comprises, as well as HPA, generally additionally water, and also other further organic compounds, for example unconverted reactants or by-products from the aldolization. Examples of other organic compounds are acetals, hemiacetals, methanol, ester, amine formate, etc. The water is supplied to the reaction system generally via the metered addition of formaldehyde, since formaldehyde is generally used as an aqueous solution.

The HPA-comprising stream from the aldolization, which is used in the process according to the invention, preferably comprises less than 10% by weight of NPG, more preferably less than 5% by weight of NPG and especially preferably less than 3% by weight of NPG, based on the HPA-comprising stream.

In a preferred embodiment, the discharge from the aldol reaction, after removal of the low boiler fraction, comprises no additional organic solvent, in order not to dilute the concentration of the HPA in the HPA-comprising stream. This is because a high concentration of HPA in the hydrogenation feed enables smaller dimensions of the hydrogenation reactor and the use of smaller amounts of catalyst, which allows the capital and operating costs to be reduced overall.

After removal of the low boiler fraction, the composition of the HPA-comprising stream from the aldolization, which is used in the process according to the invention, is preferably:
  50 to 85% by weight of HPA;
  15 to 50% by weight of water;
  Remainder: other organic compounds,
  and more preferably
  60 to 80% by weight of HPA;
  20 to 40% by weight of water,
  Remainder: other organic compounds.

As detailed above, it is also possible to use an HPA-comprising stream which comprises less than 50% by weight of HPA. As explained above, such an HPA-comprising stream is preferably used when the pH regulator is supplied to the HPA-comprising stream.

Additionally supplied in the process according to the invention is a stream which comprises NPG. In the context of the present invention, this stream is also referred to as NPG-comprising stream.

The NPG-comprising stream comprises preferably more than 30% by weight of NPG, more preferably 40 to 95% by weight, even more preferably 50 to 90% by weight and especially preferably 60 to 80% by weight.

The NPG-comprising stream typically comprises, as well as NPG, additionally water, and also other further organic compounds, for example unconverted reactants or by-products from the aldolization, or hydrogenation products thereof. Examples of other organic compounds are acetals, hemiacetals, methanol, ester, amine formate, etc.

In a very particularly preferred embodiment, NPG-comprising stream is a substream from the discharge from the hydrogenation reactor.

This substream comprises preferably
10 to 50% by weight of water,
50 to 90% by weight of NPG,
Remainder: other organic compounds,
and most preferably
20 to 40% by weight of water,
60 to 80% by weight of NPG,
Remainder: other organic compounds.

However, the NPG-comprising stream used may also be a stream which comprises purified NPG and preferably water; for example, it is possible to use NPG which has been purified by distillation in one or more stages.

According to the invention, the HPA-comprising stream and the NPG-comprising stream are combined to a hydrogenation feed.

The particular feed rates are adjusted such that the weight ratio of HPA to NPG in the hydrogenation feed is in the range from 1:100 to 50:100, preferably in the range from 3:100 to 25:100, more preferably in the range from 5:100 to 20:100, especially preferably in the range from 7:100 to 19:100 and even more preferably in the range from 8:100 to 18:100.

According to the invention, the proportion of HPA and NPG in the hydrogenation feed is at least 50% by weight, preferably at least 60% by weight, more preferably at least 65% by weight and especially preferably at least 70% by weight, based on the hydrogenation feed supplied.

In a preferred embodiment, such a hydrogenation feed can be obtained when the NPG-comprising stream used is a substream from the discharge of the hydrogenation reactor, and the weight ratio of HPA-comprising stream to NPG-comprising stream is in the range from 3:100 to 20:100, more preferably in the range form 5:100 to 15:100.

The concentrations of NPG and/or HPA in the HPA-comprising stream or in the NPG-comprising stream or in the hydrogenation feed can be determined by means of methods known to those skilled in the art. For this purpose, for example, the composition of the particular streams can be determined and the combination of the streams can be performed such that the inventive composition of the hydrogenation feed is obtained. The flow rates can be controlled, for example, by means of regulating valves or metering pumps. The measurement of the flows can generally be undertaken with customary mass flow meters.

According to the invention, one or more pH regulators are additionally supplied, in order to establish a pH of 7.0 to 9.0 at the outlet of the hydrogenation reactor.

The pH regulator used is one or more substances selected from the group consisting of tertiary amine, an inorganic base, an inorganic acid and an organic acid.

The tertiary amines used may be amines as described, for example, in DE-A 28 13 201 and DE A 27 02 582. Particular preference is given to tri-n-alkylamines, especially triethylamine, tri-n-propylamine, tri-n-butylamine and trimethylamine.

Very particular preference is given to trimethylamine (TMA), triethylamine (TEA) and tri-n-propylamine (TPA), since these compounds generally have a lower boiling point than the polymethylols formed preferentially, and hence the distillative removal from the reaction mixture is facilitated.

Trimethylamine (TMA) is especially preferably used as the tertiary amine in the reaction.

The tertiary amine used is particularly advantageously the same tertiary amine which has already been used beforehand in the aldolization stage as the catalyst.

The inorganic bases used are preferably carbonates, hydrogencarbonates and hydroxides of the alkali metals and alkaline earth metals, more preferably $Na_2CO_3$, $K_2CO_3$, $CaCO_3$, $NaHCO_3$, $KHCO_3$, NaOH, KOH and $Ca(OH)_2$. Inorganic bases can be used as a solution, preferably as an aqueous solution, preferably in a concentration of 5 to 50% by weight.

According to the invention, the inorganic or organic acids used may be mineral acids such as sulfuric acid or phosphoric acid, or organic acids such as citric acid, acetic acid or ethylhexanoic acid. Preference is given to using acetic acid.

The amount of pH regulator which is supplied to the HPA-comprising stream is selected such that the hydrogenation discharge which is withdrawn downstream of the reactor outlet has a pH of 7.0 to 9.0.

In general, in the process according to the invention, up to 1% by weight (based on the hydrogenation feed), preferably up to 0.75% by weight and more preferably up to 0.5% by weight of the tertiary amine is added to adjust the pH to the inventive range.

The amine can be used as a pure substance or as an aqueous solution. Amines can be used particularly advantageously to adjust the pH since they faun thermally decomposable salts with formic acid, which can be cleaved again after the hydrogenation. It is thus possible to avoid occurrence of salt, and the tertiary amine can be recycled into the process.

When inorganic bases, inorganic acids or organic acids are used to adjust the pH, they can be used as a pure substance or as a solution, preferably as an aqueous solution. The concentration of the aqueous solution used is more preferably from 5 to 50% by weight. More preferably, up to 3% by weight (based on the hydrogenation feed) of a 10% aqueous solution of the acid or inorganic base is added to adjust the pH.

The pH of the hydrogenation discharge is measured at the outlet of the hydrogenation reactor generally by the known techniques, preferably with a glass electrode and a pH meter.

For example, the pH can be measured online or by means of regular sampling.

The pH is measured at the outlet of the hydrogenation reactor, the outlet typically being understood to mean an area which is beyond the catalyst packing/bed or beyond the catalyst removal. The pH is preferably measured at or just downstream of the outlet from the hydrogenation reactor. The measurement may take place, for example, in a separate pumped circulation system or sampling circuit which is just beyond the outlet from the hydrogenation reactor. When the hydrogenation is performed in a plurality of reactors connected in series, for example in 2 to 4 reactors, the pH is measured at the outlet of the last hydrogenation reactor.

The amount of pH regulator supplied is generally controlled via the measurement of the pH in the hydrogenation discharge, which is preferably effected online. In general, the amount of pH regulator is regulated such that the pH in the hydrogenation discharge is within the inventive range. The pH regulator can be metered in, for example, by means of customary regulating valves and metering pumps.

According to the invention, the pH regulators can be supplied to the HPA-comprising stream or to the NPG-comprising stream or to the hydrogenation feed.

In a preferred embodiment, the pH regulator is supplied to the NPG-comprising stream.

Figure 1:
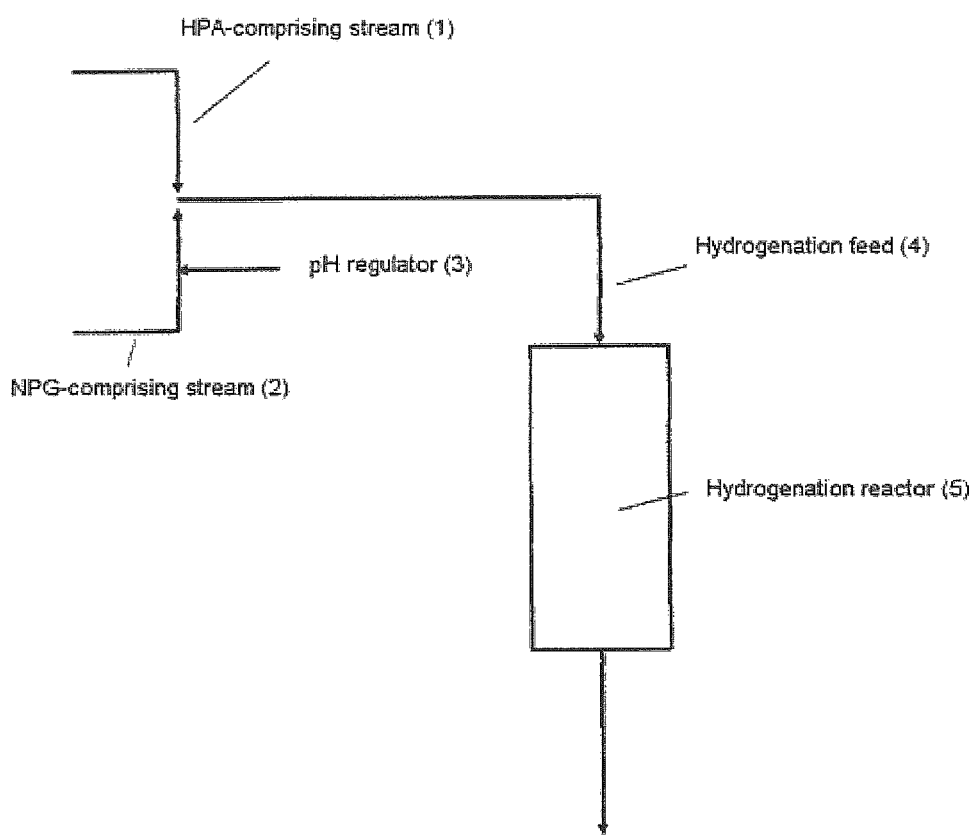
FIG. 1 depicts an embodiment of the process of the present invention wherein the pH regulator is supplied to the NPG-comprising stream.

One such embodiment is illustrated by way of example in FIG. 1. In this embodiment, the HPA-comprising stream (1) is combined with an NPG-comprising stream (2) to give a hydrogenation feed (4). The hydrogenation feed (4) is then introduced into the hydrogenation reactor (5). Before the combination of the NPG-comprising stream (2) with the HPA-comprising stream (1), a pH regulator (3) is supplied to the NPG-comprising stream.

The amount of pH regulator (3) supplied is, as described above, selected such that a pH of 7.0 to 9.0 is established at the reactor outlet.

The temperature of the NPG-comprising stream before the supply of the pH regulator is preferably in the range from 50 to 140° C., more preferably in the range from 70 to 135° C. and especially preferably in the range from 85 to 130° C.

As described above, the amount of NPG supplied is selected such that the weight ratio of HPA to NPG in the hydrogenation feed is in the range from 1:100 to 50:100, preferably in the range from 3:100 to 25:100, more preferably in the range from 5:100 to 20:100, especially preferably in the range from 7:100 to 19:100 and even more preferably in the range from 8:100 to 18:100.

Figure 2:
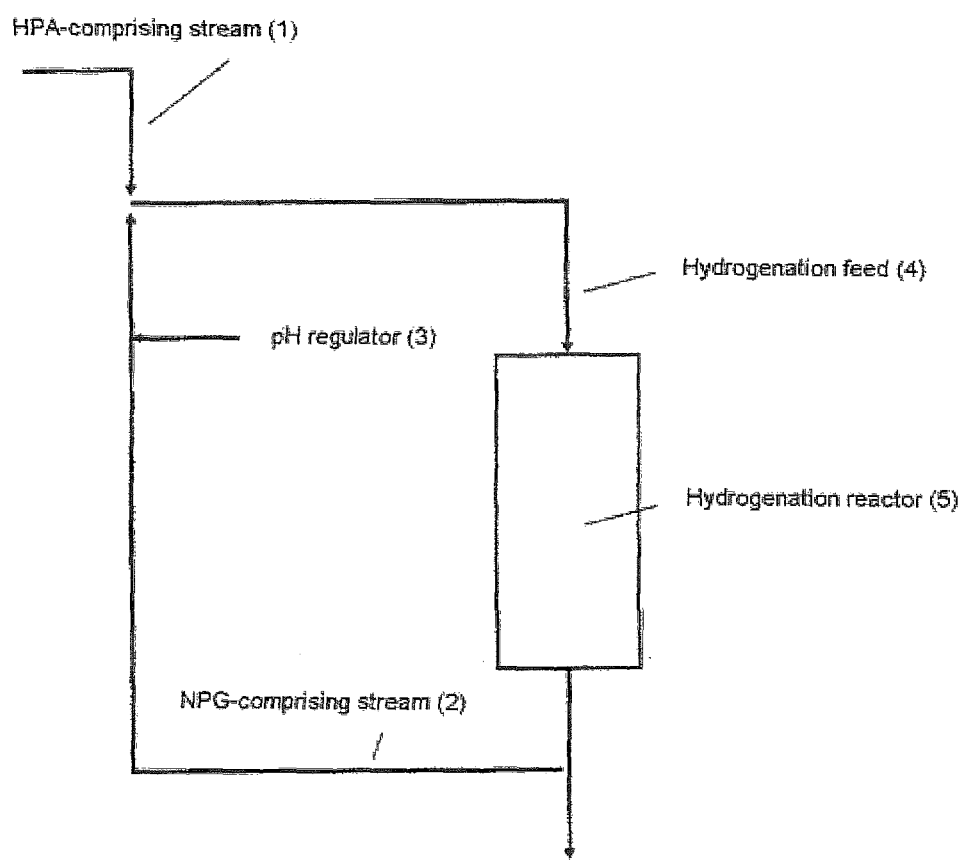
FIG. 2 depicts an embodiment of the process of the present invention wherein the NPG-comprising stream is part of the discharge from the hydrogenation reactor.

In a very particularly preferred embodiment, the NPG-comprising stream is part of the discharge from the hydrogenation reactor. This embodiment is illustrated by way of example in FIG. 2. In this embodiment, the hydrogenation discharge is split into two streams, one of which is combined as the NPG-comprising stream (2) with the HPA-comprising stream (1) to give the hydrogenation feed (4). The NPG-comprising stream, which is a substream of the reactor discharge, is also referred to in the context of the present invention as the circulation stream. In this preferred embodiment, the pH regulator (3) is supplied to the NPG-comprising circulation stream (2). The weight ratio of HPA-comprising stream (1) and NPG-comprising stream (circulation stream) (2) is, in this preferred embodiment, preferably in the range from 3:100 to 20:100, more preferably in the range from 5:100 to 15:100. The temperature of the circulation stream at the outlet from the hydrogenation reactor is generally in the range from 50 to 180° C., preferably 90 to 140° C. The circulation stream can be cooled to the abovementioned temperature range, for example by means of a heat exchanger.

In a further preferred embodiment, the pH regulator is supplied to the hydrogenation feed.

Figure 3:
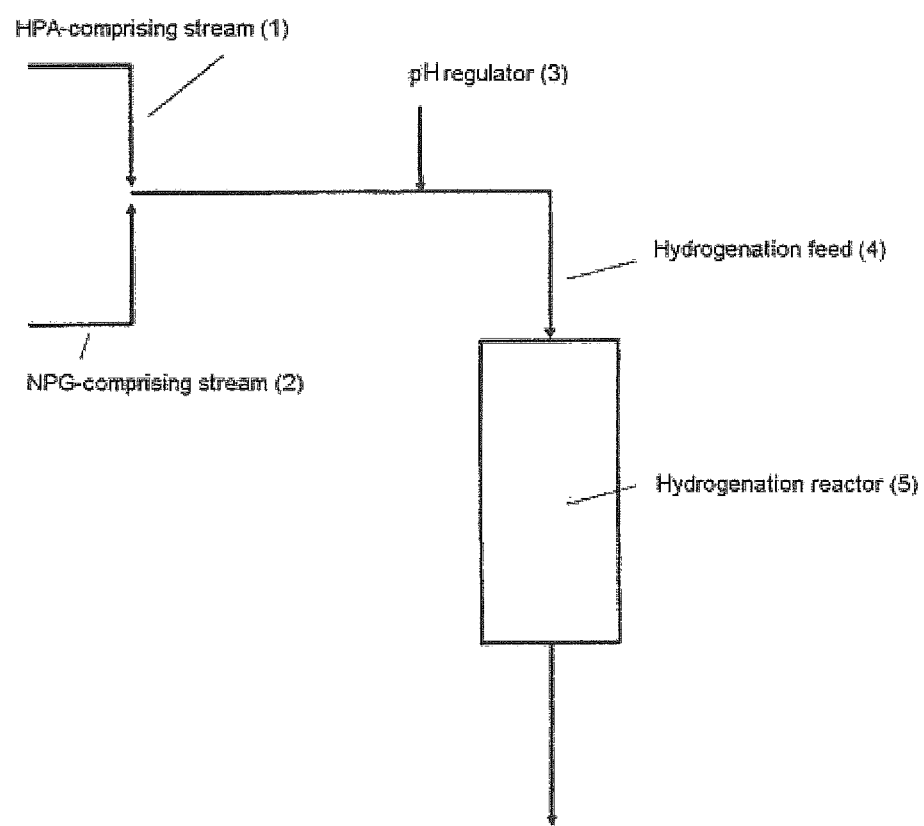
FIG. 3 depicts an embodiment of the process of the present invention wherein the pH regulator is supplied to the hydrogenation feed.

Such an embodiment is illustrated, for example, in FIG. 3.

In this embodiment, the HPA-comprising stream (1) is first combined with the NPG-comprising stream (2) to give a hydrogenation feed (4). Before the supply of the hydrogenation feed (4) to the hydrogenation reactor (5), in this preferred embodiment, a pH regulator (3) is supplied to the hydrogenation feed (4).

The amount of pH regulator (3) supplied is, as described above, selected such that a pH of 7.0 to 9.0 is established at the reactor outlet.

The temperature of the hydrogenation feed before the supply of the pH regulator is preferably in the range from 50 to 140° C., more preferably in the range from 70 to 135° C. and most preferably in the range from 85 to 130° C.

As described above, the amount of NPG supplied is selected such that the weight ratio of HPA to NPG in the hydrogenation feed is in the range from 1:100 to 50:100, preferably in the range from 3:100 to 25:100, more preferably in the range from 5:100 to 20:100, especially preferably in the range from 7:100 to 19:100 and even more preferably in the range from 8:100 to 18:100.

Figure 4:
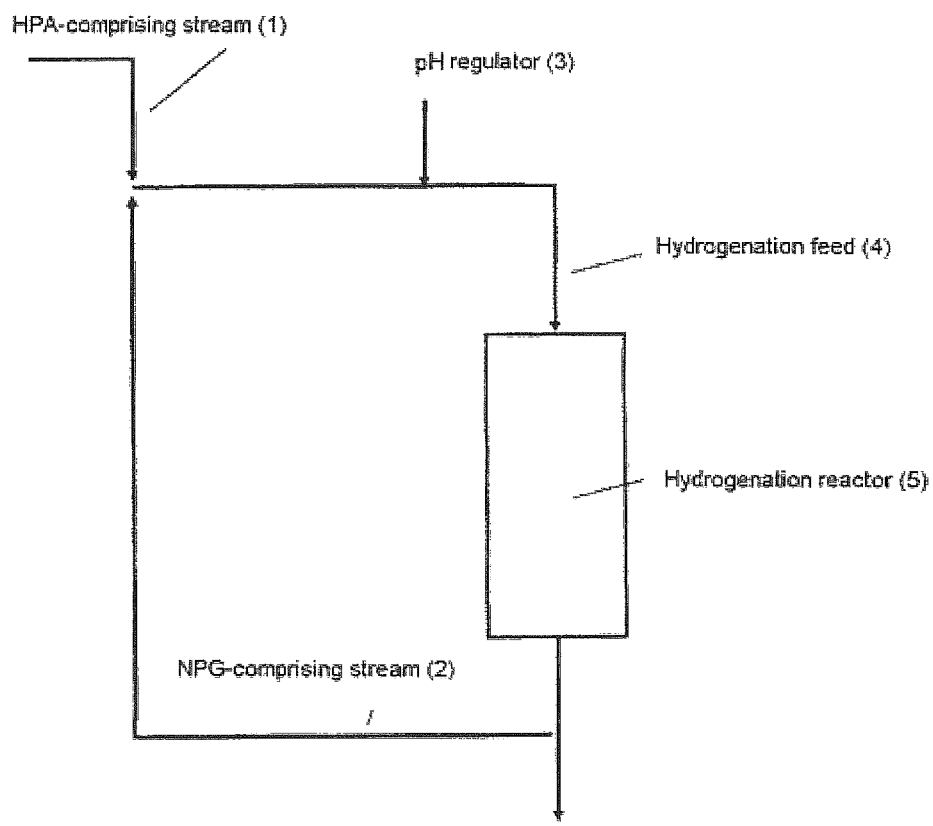
FIG. 4 depicts an embodiment of the process of the present invention wherein the NPG-comprising stream is part of the discharge from the hydrogenation reactor.

In a very particularly preferred embodiment, the NPG-comprising stream is part of the discharge from the hydrogenation reactor. This embodiment is illustrated by way of example in FIG. 4. In this embodiment, the hydrogenation discharge is split into two streams, one of which is combined as the NPG-comprising stream (2) with the HPA-comprising stream (1) to give the hydrogenation feed (4). The NPG-comprising stream, which is a substream of the reactor discharge, is also referred to in the context of the present invention as the circulation stream. In this preferred embodiment, the pH regulator (3) is supplied to the hydrogenation feed (4). The weight ratio of HPA-comprising stream (1) and NPG-comprising stream (circulation stream) (2) is, in this preferred embodiment, preferably in the range from 3:100 to 20:100, more preferably in the range from 5:100 to 15:100. The temperature of the circulation stream at the outlet from the hydrogenation reactor is generally in the range from 80 to 180° C., preferably 90 to 140° C. The circulation stream can be cooled to the abovementioned temperature range, for example by means of a heat exchanger.

In a further embodiment of this invention, the pH regulator can also be supplied to the HPA-comprising stream.

Figure 5:
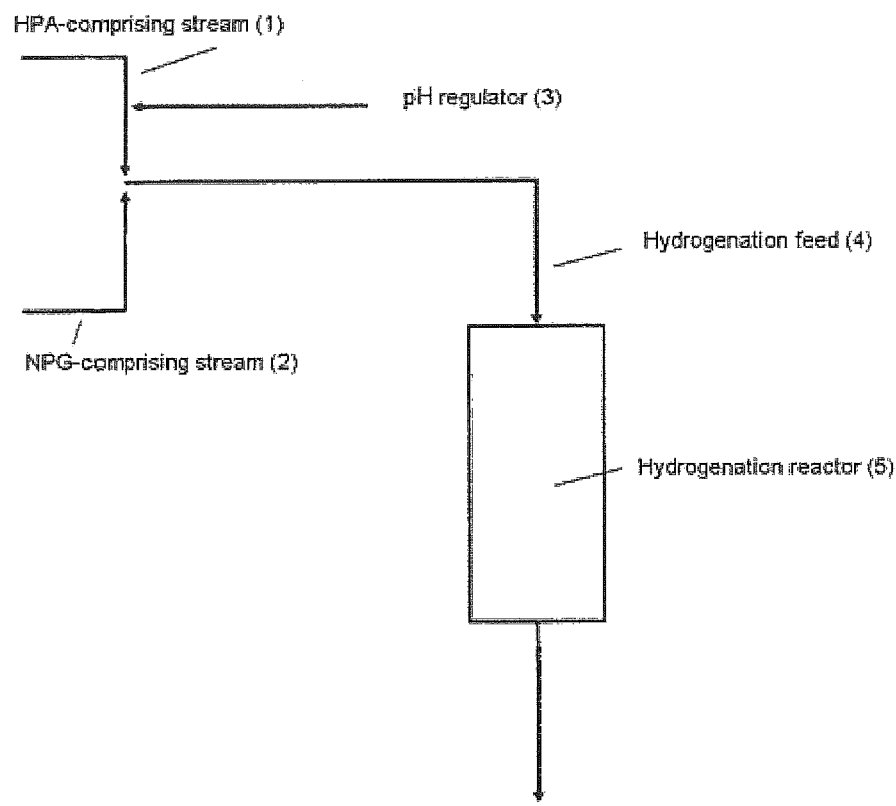
FIG. 5 depicts an embodiment of the process of the present invention wherein the pH regulator is supplied to the HPA-comprising stream.

Such an embodiment is illustrated, for example, in FIG. 5. In this embodiment, the pH regulator (3) is first supplied to the HPA-comprising stream (1), before the HPA-comprising stream (1) is combined with the NPG-comprising stream (2) to give the hydrogenation feed (4).

In this embodiment, it has to be ensured—as described above—that the concentration of the HPA in the HPA-comprising stream is low or the temperature of the HPA-comprising stream on supply of the pH regulator is low or the residence time between the supply of the pH regulator and the subsequent supply of the NPG-comprising stream is short.

When the weight ratio of HPA in the HPA-comprising stream before the supply of the pH regulator is less than 50% by weight, preferably less than 40% by weight and more preferably less than 30% by weight, the temperature in the HPA-comprising stream on supply of the pH regulator is preferably in the range from 50 to 100° C., more preferably in the range from 60 to 80° C., though the temperature should not be selected at such a low level that the HPA in the HPA-comprising stream solidifies. The residence time between the supply of the pH regulator and the combination of the HPA-comprising stream with the NPG-comprising stream to give the hydrogenation feed may in this case be more than 5 minutes, but the residence time is preferably 1 to 30 minutes, more preferably 3 to 15 minutes.

When the weight ratio of HPA in the HPA-comprising stream before the supply of the pH regulator is more than 50% by weight, the temperature of the HPA-comprising stream before the supply of the pH regulator should preferably be less than 75° C., more preferably less than 70° C., though it should be ensured that the temperature is not selected at such a low level that the HPA in the HPA-comprising stream solidifies. The residence time between the supply of the pH regulator and the combination of the HPA-comprising stream with the NPG-comprising stream to give the hydrogenation feed may in this case be more than 5 minutes, but the residence time is preferably 1 to 30 minutes, more preferably 3 to 15 minutes.

When the weight ratio of HPA in the HPA-comprising stream before the supply of the pH regulator is more than 50% by weight and the temperature of the HPA-comprising stream before the supply of the pH regulator is more than 60° C., the residence time between the supply of the pH regulator and the combination of the HPA-comprising stream with the NPG-comprising stream to give the hydrogenation feed should be less than 5 minutes, more preferably less than 3 minutes and most preferably less than 1 minute.

As described above, the amount of NPG supplied is selected such that the weight ratio of HPA to NPG in the hydrogenation feed is in the range from 1:100 to 50:100, preferably in the range from 3:100 to 25:100, more preferably in the range from 5:100 to 20:100, especially preferably in the range from 7:100 to 19:100 and even more preferably in the range from 8:100 to 18:100.

The amount of pH regulator (3) supplied is, as described above, selected such that a pH of 7.0 to 9.0 is established at the reactor outlet.

Figure 6:
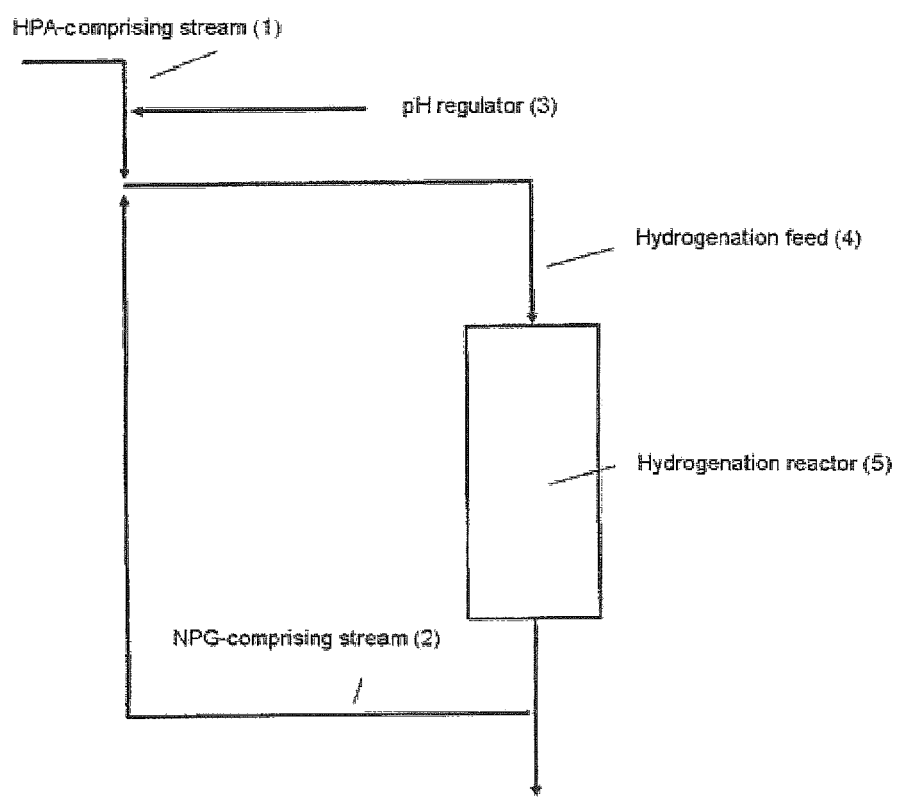
FIG. 6 depicts an embodiment of the process of the present invention wherein the NPG-comprising stream is part of the discharge from the hydrogenation reactor.

In a preferred embodiment, the NPG-comprising stream is part of the discharge from the hydrogenation reactor. This embodiment is illustrated by way of example in FIG. 6. In this embodiment, the reaction discharge is split into two streams, one of which is combined as the NPG-comprising stream (2) with the HPA-comprising stream (1) to give the hydrogenation feed (4). The NPG-comprising stream, which is a substream of the reactor discharge, is also referred to in the context of the present invention as the circulation stream. In this embodiment, the pH regulator (3) is supplied to the HPA-comprising stream (1). The weight ratio of HPA-comprising stream (1) and NPG-comprising stream (circulation stream) (2) is, in this preferred embodiment, preferably in the range from 3:100 to 20:100, more preferably in the range from 5:100 to 15:100.

The temperature of the circulation stream at the outlet from the hydrogenation reactor is generally in the range from 50 to 180° C., preferably 90 to 140° C. The circulation stream can be cooled to the abovementioned temperature range, for example by means of a heat exchanger.

These embodiments, in which the pH regulator is supplied to the HPA-comprising stream, are less preferred than the abovementioned preferred embodiments in which the pH regulator is supplied to the NPG-comprising stream or to the hydrogenation feed, but enable the same technical advantages.

The hydrogenation of HPA is effected in one or more reactors with hydrogen in the presence of a hydrogenation catalyst.

The catalysts used may preferably be catalysts which preferably comprise at least one metal of transition groups 8 to 12 of the periodic table of the elements, such as Fe, Ru, Os, Co, Rh, Ir, Ni, Pd, Pt, Cu, Ag, Au, Zn, Cd, Hg, preferably Fe, Co, Ni, Cu, Ru, Pd, Pt, more preferably Ni and Cu and especially preferably Cu, preferably on a customary support material, more preferably on one from the oxides of titanium, of zirconium, of hafnium, of silicon and/or of aluminum. The catalysts useable in accordance with the invention can be prepared by processes known from the prior art for preparation of such supported catalysts. It is also possible with preference to use supported catalysts which comprise copper on an aluminum oxide- or titanium dioxide-containing support material in the presence or absence of one or more of the elements magnesium, barium, zinc or chromium. Such catalysts and the preparation thereof are known from WO 99/44974.

Additionally suitable for the inventive hydrogenation are supported copper catalysts as described, for example, in WO 95/32171, and the catalysts disclosed in EP-A 44 444 and DE 19 57 591.

The hydrogenation is performed continuously in one or more hydrogenation reactors.

The reactor used is preferably a reactor tube filled with a catalyst bed, in which the reaction solution is passed over the catalyst bed, for example in trickle mode or liquid phase mode, as described in DEA 19 41 633 or DEA 20 40 501.

However, the reactor used may also be a continuous stirred tank reactor.

In a preferred embodiment, the hydrogenation is performed in a hydrogenation reactor which consists of two or more reactors connected in series, for example in a stirred tank cascade or in a plurality of tubular reactors connected in series.

Particular preference is given to performing the hydrogenation in two to four, more preferably 2, tubular reactors connected in series, in which case the hydrogenation reaction in the individual reactors before the last reactor is performed only up to a partial conversion of, for example, 50 to 98%, and only in the last reactor is the hydrogenation completed. In a further preferred embodiment, a substream of the reaction discharge, optionally while cooling, is returned and recycled back into the reactor. The substream from the first hydrogenation reactor is more preferably returned as a circulation stream. This circulation method is preferably conducted with a ratio of feed (HPA-comprising stream) to circulation (NPG-comprising circulation stream) of 3:100 to 20:100 and more preferably in the range from 5:100 to 15:100.

The hydrogenation temperature is generally between 50 and 180° C., preferably 90 and 140° C. The hydrogenation pressure employed is generally 10 to 250 bar, preferably 20 to 120 bar.

The hydrogenation can be performed with addition of an inert solvent. Useable diluents are water, cyclic ethers such as THF or dioxane, or else acyclic ethers, and likewise lower alcohols, for example methanol, ethanol or 2-ethylhexanol.

However, preference is given to effecting the hydrogenation without addition of inert solvents since, as described above, an addition of solvent would reduce the concentration of HPA in the hydrogenation feed.

The process according to the invention makes it possible to reduce side reactions in the hydrogenation, to increase the selectivity of the conversion of HPA to NPG and to enhance the yield of NPG. In the conversion of hydroxypivalaldehyde to NPG, it is possible, for example, to reduce the formation of hydroxypivalic acid (HPA).

By means of the process according to the invention, it is also possible to prepare NPG with a high yield over a long period, which means that the service life of the catalysts used is increased and exchange of the catalysts used is required less often. Furthermore, the amount of the pH regulators added can be reduced in order to reduce the amount of raw materials used.

The invention is illustrated by the examples which follow:

EXAMPLE 1

Preparation of an HPA-Comprising Stream 1.1 mol of isobutyraldehyde was stirred with 1 mol of formaldehyde in the form of a 49% solution and 4 mol % of trimethylamine, based on isobutyraldehyde, at 70-75° C. for 1.5 h. The reaction solution was concentrated by distilling off low boilers, for example isobutyraldehyde and amine, at standard pressure. The bottoms obtained consisted of 70% by weight of hydroxypivalaldehyde, 25% by weight of water and approx. 5% by weight of other organic secondary components.

EXAMPLE 2 (COMPARATIVE EXPERIMENT)

Hydrogenation of the HPA-Comprising Stream from Example 1

The HPA-comprising stream used was the mixture prepared according to example 1.

This HPA-comprising stream was first passed into a hydrogenation reactor which was operated in trickle mode at $H_2$ pressure 37-40 bar and at 100-120° C. The hourly space velocity was 0.28 kg of solution/(l cat.*h). The catalyst used was a $Cu/Al_2O_3$ catalyst as described in EP-A-44444 or WO-A-2007/042456, which was activated according to the disclosure of EP-A-44444 or WO-A-2007/042456 in a tubular reactor at 190° C. at ambient pressure by passing a mixture of 5% by volume of hydrogen and 95% by volume of nitrogen (total volume 50 l (STP)/h) over it for 24 h.

The hydrogenation discharge was split into two substreams.

In steady-state operation, one substream as the NPG-comprising circulation stream was combined with the HPA-comprising stream.

The ratio of NPG-comprising circulation stream to the HPA-comprising stream from example 1 was approx. 10:1.

The composition of the circulation stream was 25% by weight of water, 68% by weight of NPG, 1.6% by weight of HPA, remainder (approx. 6% by weight) other organic compounds.

The hydrogenation feed thus obtained was subsequently introduced into the hydrogenation reactor.

The composition of the hydrogenation feed was 25% by weight of water, 64% by weight of NPG, 7% by weight of HPA and 4% by weight of other organic compounds.

The weight ratio of HPA to NPG in the hydrogenation feed was approx. 1:9.

The portion of the hydrogenation discharge which was not recycled as the NPG-comprising circulation stream was conducted through a second hydrogenation reactor.

The second hydrogenation reactor was operated at 37-40 bar and a temperature of 110-130° C. The catalyst used was the same catalyst as in the first hydrogenation reactor.

A pH of approx. 8 was established in the discharge of the second reactor, by adding trimethylamine (TMA) (pH regulator) to the HPA-comprising stream from example 1.

The pH regulator was supplied before the combination of the HPA-comprising stream with the NPG-comprising circulation stream.

The temperature of the HPA-comprising stream from example 1 on supply of the pH regulator (TMA) was 80° C. The residence time between the addition of the pH regulator and the supply of the circulation stream was 10 minutes (>5 minutes).

EXAMPLE 3 (INVENTIVE EXAMPLE)

Hydrogenation of the HPA-Comprising Stream from Example 1

The hydrogenation was effected under the same conditions as in example 2. To establish a pH of 8 at the outlet of the second reactor, the pH regulator (TMA) was, however, supplied directly to the NPG-comprising circulation stream before the NPG-comprising stream was combined with the HPA-comprising stream from example 1. The weight ratio of HPA to NPG in the hydrogenation feed obtained by combining these streams was approx. 1:9.

The composition of the hydrogenation feed was 25% by weight of water, 64% by weight of NPG, 7% by weight of HPA and 4% by weight of other organic compounds.

Table 1 shows conversions, selectivities and the HPAc content after the hydrogenation for examples 2 and 3. The conversions were determined by means of gas chromatography (GC method: column: 50 m Chrompack CP-Sil 8 CB, diameter 0.53 mm, FD 5.0, temperature program: 5 min 50° C. isothermal, then heat at 20° C. per min to 200° C., hold isothermal for 17.5 min Injector: 250° C., FID detector: 300° C. Flow 3.8 ml/min, split: 20).

TABLE 1

| Addition of TMA | pH of feed | pH of hydrogenation output | HPAc after hydrogenation [GC area %] | TMA consumed g/kg of IBa | Temperature on metered addition [° C.] | Conversion [%] | Selectivity [%] |
|---|---|---|---|---|---|---|---|
| Example 2 | 8.2 | 7.9 | 0.625 | 15.1 | 80 | 99.2 | 97.6 |
| Example 3 | 8.0 | 8.2 | 0.042 | 5.55 | 107 | 99.9 | 98.9 |

The invention claimed is:

1. A process for preparing neopentyl glycol (NPG) by continuously hydrogenating hydroxypivalaldehyde (HPA)

with hydrogen, in the liquid phase, in the presence of a hydrogenation catalyst, in a hydrogenation reactor, by combining an HPA-comprising stream with an NPG-comprising stream to give a hydrogenation feed and introducing the hydrogenation feed into the hydrogenation reactor and additionally supplying at least one pH regulator selected from the group consisting of tertiary amine, an inorganic base, an inorganic acid and an organic acid to the HPA-comprising stream or the NPG-comprising stream or the hydrogenation feed, in order to establish a pH of 7.0 to 9.0 at the outlet of the hydrogenation reactor, wherein the weight ratio of HPA to NPG in the hydrogenation feed is in the range from 1:100 to 50:100 and the proportion of HPA and NPG in the hydrogenation feed is at least 50% by weight, based on the hydrogenation feed, and the NPG-comprising stream comprises more than 30% by weight up to 80% by weight of NPG and 20 to 40% by weight of water., and, in the case that the pH regulator is supplied to the HPA-comprising stream, the HPA-comprising stream comprises less than 50% by weight of HPA.

2. The process according to claim 1, wherein the pH regulator is supplied to the NPG-comprising stream.

3. The process according to claim 1, wherein the pH regulator is supplied to the hydrogenation feed.

4. The process according to claim 1, wherein the HPA-comprising stream comprises 50 to 85% by weight of HPA, 15 to 50% by weight of water, remainder: other organic compounds.

5. The process according to claim 1, wherein the NPG-comprising stream comprises 50 to 80% by weight of NPG.

6. The process according to claim 1, wherein the weight ratio of HPA to NPG in the hydrogenation feed is in the range from 3:100 to 25:100.

7. The process according to claim 1, wherein the pH regulator is trimethylamine.

8. The process according to claim 1, wherein the NPG-comprising stream is a substream from the discharge of the hydrogenation reactor.

9. The process according to claim 1, wherein the hydrogenation is performed in two or more hydrogenation reactors connected in series.

* * * * *